United States Patent [19]
Barrett

[11] Patent Number: 5,955,025
[45] Date of Patent: Sep. 21, 1999

[54] CHEMICAL VAPOR STERILIZATION INDICATING MATERIALS

[75] Inventor: Richard B. Barrett, Chatham, N.J.

[73] Assignee: Tempil, Inc., South Plainfield, N.J.

[21] Appl. No.: 08/841,311

[22] Filed: Apr. 30, 1997

[51] Int. Cl.⁶ ........................................................ A61L 2/20
[52] U.S. Cl. ................................ 422/28; 422/55; 422/83; 422/86; 422/87; 422/119; 422/292; 116/206; 252/408.1; 436/1; 436/135
[58] Field of Search .................................. 422/28, 55–57, 422/83, 86, 87, 119, 292; 116/206; 252/408.1; 436/135, 1

[56] References Cited

U.S. PATENT DOCUMENTS

| | | | |
|---|---|---|---|
| 5,139,957 | 8/1992 | Grack | 436/135 |
| 5,352,282 | 10/1994 | Miller | 106/22 B |
| 5,556,743 | 9/1996 | Gibboni et al. | 435/4 |
| 5,741,460 | 4/1998 | Jacob et al. | 422/28 |

FOREIGN PATENT DOCUMENTS

| | | |
|---|---|---|
| 2022194 | 3/1974 | France . |
| 108767 | 4/1980 | Poland . |

OTHER PUBLICATIONS

Nakagawa et al., "Characteristic bleaching profiles of cyanine dyes depending on active oxygen species in the controlled Fenton reaction.", Biol. Pharm. Bull., 16(11), 1061–1064. (abstract), 1993.

*Primary Examiner*—Terrence R. Till
*Assistant Examiner*—Fariborz Moazzam
*Attorney, Agent, or Firm*—Burns, Doane, Swecker & Mathis. L.L.P.

[57] ABSTRACT

Provided is a system for indicating exposure to a chemical vapor sterilization process. This system comprises a composition applied to a suitable support, which composition comprises a component which is chromatically transformed by the action of a vapor phase sterilant. In particular, the present invention is applicable to a system for indicating exposure to a hydrogen peroxide vapor sterilization process, with the component which is chemically transformed being so transformed in the presence of vaporous hydrogen peroxide. The composition comprises at least the component which is chemically transformed by the action of the hydrogen peroxide, but may also contain additional ingredients or components. For example, the composition also generally comprises a binder to aid in applying the composition to a suitable support or substrate. As well, the composition can contain a second dye material, generally one which maintains its characteristic color in the presence of the vaporous chemical sterilant which chromatically transforms the first dye component.

25 Claims, No Drawings

CHEMICAL VAPOR STERILIZATION INDICATING MATERIALS

BACKGROUND OF THE INVENTION

1. Field of the Invention

The present invention relates to a system and composition useful in indicating the occurrence of chemical vapor sterilization. More particularly, the present invention relates to a composition which undergoes a change in appearance when exposed to the hydrogen peroxide used in a chemical vapor sterilization process.

2. Brief Description of the Prior Art

Methods using steam and disinfecting gases, particularly ethylene oxide, have been widely used for sterilizing medical products ranging from pharmaceutical preparations to surgical instruments. A sterilizing method must effectively render all microbial organisms non-viable without damage to the article or goods being sterilized or its packaging. However, many disinfecting gases which meet this criteria, such as ethylene oxide, have been recognized to expose workers and the environment to safety hazards. As a result, alternative methods have emerged, among which are the low temperature chemical vapor phase sterilization techniques.

The recent emergence of chemical vapor phase sterilization technology operating well below temperatures associated with steam sterilization has created the need for new indicator materials/systems. These "low temperature" technologies, operating below 176° F., and generally below 150° F., share a common property that the sterilized goods are available for use shortly after the completion of the sterilization cycle. This property distinguishes these sterilization processes from sterilization by ethylene oxide, which also operates in the specified temperature range, but requires lengthy aeration of the sterilized goods due to the toxicity of residual ethylene oxide. In contrast, the new processes are intended to rely heavily on the presence of hydrogen peroxide whose non-toxic decomposition products are water and oxygen. The potency of the hydrogen peroxide may be augmented by the presence of peracetic acid and/or electrical energy in the form of an ionizing plasma field.

There exist a variety of indicating compositions, and coated media, for visualization of the presence of aqueous solutions of hydrogen peroxide. For example, U.S. Pat. No. 3,183,173 teaches the use of filter paper impregnated with iodide and molybdate salts in a buffered polyvinyl alcohol solution. The paper is useful for the detection of aqueous solutions of hydrogen peroxide.

See also, Diebold, Rapkin and Usmani (Chemtech, August 1991, pp. 462–465), who describe systems such as hydrogen peroxide-tetramethylbenzidine and hydrogen peroxide, 4-aminoantipyrine and phenol which yield color products useful for determining the presence of glucose and cholesterol. In both cases hydrogen peroxide is a product of the reaction of the analytes (glucose or cholesterol) and thus its detection is a secondary measure of the analytes.

U.S. Pat. Nos. 5,326,388, 5,352,282, 5,486,228 and 5,492,558 describe the selective high pH bleaching of coated materials by liquid reactants including hydrogen sulfide, sodium sulfite, sodium hypochlorite, and hydrogen peroxide. In particular, the patents describe a multiple coloring composition system whose coloring effect is changed upon treatment with a second coloring composition upon depositing the second coloring composition over the first coloring composition. The first coloring composition comprises a dye whose coloring ability is destroyed in the presence of a bleach. The second coloring composition, which is used to change the coloring effect of the first composition, contains bleach and a colorant capable of maintaining its characteristic color in the presence of the bleach. Among the dyes found in the bleachable coatings are Astrazon Brilliant Red 4G (Basic Red 14) and Astrazon Pink FBB (Basic Red 49).

A suitable indicator imminently useful with the new chemical vapor phase sterilization processes would be valuable to the industry.

Accordingly, it is an objective of the present invention to provide a color change composition useful in indicator materials for indicating the vapor phase sterilization of an article.

It is yet another object of the present invention to provide systems for indicating vapor phase sterilization of an article, employing such color change compositions.

Yet another object of the present invention is to provide a process for indicating when an article has been subjected to a sterilization process.

These and other objects of the present invention will become apparent upon a review of the following specification and the claims appended thereto.

SUMMARY OF THE INVENTION

In accordance with the foregoing objectives, there is provided a system for indicating exposure to a vapor sterilization process. This system comprises a composition applied to a suitable support, which composition comprises a component which is chromatically transformed by the action of a vapor phase sterilant. In particular, the present invention is directed to a system for indicating exposure to a hydrogen peroxide vapor sterilization process, with the component which is chemically transformed being so transformed in the presence of vaporous hydrogen peroxide. The composition comprises at least the component which is chemically transformed by the action of the hydrogen peroxide, but may also contain additional ingredients or components. For example, the composition also generally comprises a binder to aid in applying the composition to a suitable support or substrate. As well, the composition can contain a second dye material, generally one which maintains its characteristic color in the presence of the vaporous chemical sterilant which chromatically transforms the first dye component.

The system of the present invention is very useful in indicating when an article has been exposed to a sterilization process using the vapor phase sterilization technology of today. Since the technology has primarily been using hydrogen peroxide as the chemical sterilant, the present invention preferably employs components which are chromatically transformed in the presence of hydrogen peroxide. Such components generally involve dyes, such as cyanine dyes or metallized reactive dyes, e.g., copper diazo dyes.

The system and compositions of the present invention offer one a simple, yet effective means for indicating when a particular article has been subjected to vapor sterilization, particularly for sterilization using vaporous hydrogen peroxide.

DETAILED DESCRIPTION OF THE PREFERRED EMBODIMENTS

The indicating compositions of the present invention are preferably comprised of a composition comprising at least one colored component capable of being decolorized in the presence of sterilizing environments containing a vapor chemical sterilant such as vaporized hydrogen peroxide. While only one component capable of being chromatically transformed is generally necessary in the composition of the present invention, a mixture or blend of components, e.g., dyes, could be used. Such mixtures or blends would increase the options available in color changes dramatically. Preferably, the indicating composition is an aqueous dispersion of a binder, a polymeric binder, and the colored component capable of chromatic transformation.

The colored component, capable of being decolorized by the sterilizing environments, will be present in a range of about 0.1 to 14 percent by weight. The colored component generally comprises dyes, preferably soluble in water. Dyes soluble in other solvents, however, can also be used, as can pigment dispersions.

Examples of suitable decolorizable materials include the following dyes, all of which are copper containing dyes:

| Dye | Source | Start Color | Final Color |
| --- | --- | --- | --- |
| Reactive Red B | Rite Industries | Red | Pale Red |
| Reactive Blue BF4R | Rite Industries | Blue | Light Gray |
| Reactive Violet 5R | Rite Industries | Violet | Light Gray |
| Reactive Red RBS | Rite Industries | Red | Lt. Violet |

A suitable cyanine based dye which is quite suitable for the present invention is the commercially available Astrazon Brilliant Red 4GN, available from Dystar. The initial color is red, with the chromatically transformed color being light grey. Cyanine dyes such as those discussed in U.S. Pat. No. 5,352,282, which is hereby incorporated by reference, are preferred for the purposes of the present invention due to availability and ease of use. Any suitable cyanine dye can be used.

It should be further noted that the amount of dye present, or dye concentration in the indicating composition, in combination with the amount of sterilant used in the sterilization process, may affect the degree of color change observed. The dye concentration can be so great that insufficient bleaching occurs so that the color change is insufficient to register a clear indication. It has been found that at lower dye amounts or concentrations, clearer indications are more easily obtained. It is preferred, therefore, that the amount of chromatically transformed dye contained in the indicating composition of the present invention be less than 3 weight percent, more preferably less than 1 weight percent, and most preferably less than 0.3 weight percent. In effect, the dye concentration should be such as to allow a clear indication of a color change, e.g., a change of at least 0.2 units as measured by a color densitometer based on the amount of sterilant to be used.

In addition to the decolorizable component, there may also be present a colored component that is immune to the actions of the sterilizing environment. This component may be present in the range of from 0 to 15 weight percent. Any suitable component which does not lose its color in the presence of the vapor sterilant (and does not interact with the chromatically transformed component) can be used. Examples of such sterilant-immune colored components include:

| Dye Dispersion | Source | Chemical Base |
| --- | --- | --- |
| Phthalo Green | Sun Chemical | Copper Phthalocyanine |
| 613 Red | Ciba-Geigy | |
| RBH 509930 | RBH Dispersions | Arylide Yellow |
| Black Oxide | Landers-Segal | Mixed metal oxides |
| Pigment Violet 19 | Ciba-Geigy | Quinacridone red |

The indicating composition is generally formulated in the form of an aqueous dispersion. The dispersion would comprise the component which is chromatically transformed, as well as a water dispersible binder. Any suitable water dispersible binder can be used, for example, such as a polyacrylate. Generally, the dispersions will contain between about 20 and 40 weight percent of a polymer binder.

The vapor sterilization procedure used is conventional. The three types of hydrogen peroxide based procedures include Sterrad ($H_2O_2$+plasma); Plazlyte ($H_2O$+peracetic acid); and VHP ($H_2O_2$). The foregoing types of sterilization procedures are discussed in the literature, for example, in U.S. Pat. Nos. 4,756,882 and 4,643,876 (Sterrad); 5,413,760 and 5,603,895 (Plazlyte); and 4,956,145 and 5,445,792 (VHP), all of which are hereby expressly incorporated by reference.

In general, the article to be sterilized is placed in a sterilization chamber, and a dose of sterilant, which generally comes pre-measured, is delivered to the chamber. Vapor is generated and allowed to fill the container for an appropriate length of time after which the sterilization is complete. The equipment and the entire procedure is generally controlled electronically. When sterilizing medical instruments, one cycle is often sufficient. The medical instruments are often packaged, with the entire package being placed into the sterilizing compartment. The package allows the hydrogen peroxide to penetrate and effect sterilization of the instrument, while subsequently protecting the instrument from contamination in air.

The temperatures used in the process of the present invention are all generally less than 150° F. The Sterrad process, for example, is generally run at 122° F., whereas the VHP process is run at room temperature.

The invention will be illustrated in greater detail by the following specific examples. It is understood that these examples are given by way of illustration and are not meant to limit the disclosure or the claims to follow. All percentages in the examples, and elsewhere in the specification, are by weight unless otherwise specified.

EXAMPLES

Low-temperature sterilant compositions in accordance with the present invention were prepared by mixing the components together to form an aqueous dispersion. The compositions were then printed onto paper and Tyvek™ substrates using a hand proofer with a 120 anilox roll. The paper was autoclavable Kraft paper, and the Tyvek™ was grades 1059 and 1073, available from DuPont. The compositions are described below in the Table, with the amounts of each component reflecting weight percent.

Compositions for Coatings Undergoing the Noted Color Transitions When Exposed to Low Temperature Sterilizing Environment Containing Hydrogen Peroxide

| Component | Ink 101 Blue to Green | Ink 102 Blue to Red | Ink 103 Blue to Yellow | Ink 105 Blue to Gray | Ink 106 Red to Gray |
|---|---|---|---|---|---|
| Reactive Blue BF4R | 7 | 7 | 7 | 7 | |
| Red 4GN | | | | | 0.2 |
| 613 Red | | 2 | | | |
| Phthalo Green Dispersion | 10 | | | | |
| Titania Dispersion | 2 | 2 | 6 | 6 | |
| Arylide Yellow Dispersion | | | 2 | | |
| Black Oxide Dispersion | | | | 3 | |
| Binder Dispersion | 56 | 66 | 66 | 56 | 66 |
| Rheological Agent | .5 | .1 | .3 | .3 | .3 |
| Defoamers | .2 | .2 | .2 | .2 | .2 |

Note: Balance is water in the foregoing compositions, and the binder dispersions comprise about 50 wt. percent polymer solids and 50 wt. percent water.

In the following experimental runs, the sterilization process used was one of the following three as indicated:

Sterrad Sterilization: One STANDARD Cycle ($H_2O_2$+plasma)

Plazlyte Sterilization: One STANDARD Cycle ($H_2O_2$+peracetic acid+plasma)

VHP Sterilization: One STANDARD Cycle ($H_2O_2$)

Runs 1 to 9

The coated Tyvek™ substrates were presented to a sterilization medium using either the Sterrad, Plazlyte or VHP process. Following the sterilization process, the "As Printed" and Processed materials were evaluated using a reflecting densitometer capable of reporting C (cyanine), Y (yellow), M (magenta) and K (black) values. These values have a high number when little light is reflected into the densitometer (visually dark), and a low number when more light is reflected (visually light). The greater the difference (Delta) between the two values, the more visually different the samples appear. A delta of 0.20 in one or more of the values is required for visual discrimination.

In the examples reported below, coated samples were evaluated in the three types of low temperature, gas phase sterilizers: Sterrad, Plazlyte and VHP.

The results indicate that excellent visible color changes were achieved in each of the three processes when using the indicating composition of the present invention. The results are tabulated below:

Run 1: Sterrad Process

| Ink 101 | C | Y | M | K |
|---|---|---|---|---|
| Blue to Green As Printed | 1.12 | 0.75 | 0.96 | 1.02 |
| Post-Sterrad | .71 | 0.47 | 0.40 | 0.50 |
| Delta | 0.41 | 0.28 | 0.56 | 0.52 |

Run 2: Sterrad Process

| Ink 102 | C | Y | M | K |
|---|---|---|---|---|
| Blue to Red As Printed | 0.96 | 0.68 | 0.98 | 0.98 |
| Post-Sterrad | 0.30 | 0.56 | 0.76 | 0.58 |
| Delta | 0.66 | 0.32 | 0.22 | 0.40 |

Run 3: Sterrad Process

| Ink 103 | C | Y | M | K |
|---|---|---|---|---|
| Blue to Yellow As Printed | 0.97 | 0.71 | 0.85 | 0.91 |
| Post-Sterrad | 0.19 | 0.51 | 0.21 | 0.20 |
| Delta | 0.78 | 0.20 | 0.64 | 0.71 |

Run 4: Sterrad Process

| Ink 105 | C | Y | M | K |
|---|---|---|---|---|
| Blue to Gray As Printed | 1.03 | 0.69 | 0.95 | 0.99 |
| Post-Sterrad | 0.54 | 0.57 | 0.59 | 0.57 |
| Delta | 0.49 | 0.12 | 0.36 | 0.42 |

Run 5: Plazlyte Process

| Ink 102 | C | Y | M | K |
|---|---|---|---|---|
| Blue to Red As Printed | .83 | 0.70 | 0.98 | .91 |
| Post-Plazlyte | .61 | 0.66 | 0.88 | 0.79 |
| Delta | 0.22 | 0.14 | 0.10 | 0.12 |

Run 6: Plazlyte Process

| Ink 105 | C | Y | M | K |
|---|---|---|---|---|
| Blue to Gray As Printed | 0.80 | 0.53 | 0.69 | 0.73 |
| Post-Plazlyte | 0.54 | 0.46 | 0.49 | 0.51 |
| Delta | 0.26 | 0.07 | 0.20 | 0.22 |

Run 7: VHP Process

| Ink 102 | C | Y | M | K |
|---|---|---|---|---|
| Blue to Red As Printed | 0.56 | 0.52 | 0.74 | 0.68 |
| Post-VHP | 0.20 | 0.42 | 0.60 | 0.45 |
| Delta | 0.36 | 0.20 | 0.06 | 0.13 |

Run 8: VHP Process

| Ink 103 | C | Y | M | K |
|---|---|---|---|---|
| Blue to Yellow As Printed | 1.02 | 0.81 | 0.90 | 0.95 |
| Post-VHP | 0.23 | 0.63 | 0.27 | 0.25 |
| Delta | 0.79 | 0.28 | 0.63 | 0.70 |

Run 9: Sterrad Process

| Ink 106 | C | Y | M | K |
|---|---|---|---|---|
| Red to Gray As Printed | .2 | .29 | .57 | .44 |
| Post-Sterrad | .26 | .17 | .22 | .23 |
| Delta | (.06) | .12 | .35 | .21 |

While the invention has been described with preferred embodiments, it is to be understood that variations and modifications may be resorted to as will be apparent to those skilled in the art. Such variations and modifications are to be considered within the purview and the scope of the claims appended hereto.

What is claimed is:

1. A system for indicating vapor sterilization, which system comprises a composition applied to a non-cellulosic support suitable for use in a vapor phase sterilization environment, which composition comprises a component which is chromatically transformed permanently by the action of a vapor phase sterilization treatment, with said component comprising a metallized reactive dye or a cyanine dye.

2. The system of claim 1, wherein the vapor phase sterilization treatment comprises sterilization by means of hydrogen peroxide vapor.

3. The system of claim 2, wherein the component which is chromatically transformed comprises a metallized reactive dye.

4. The system of claim 3, wherein the metallized reactive dye is comprised of a copper diazo dye.

5. The system of claim 2, wherein the composition comprises a binder.

6. The system of claim 5, wherein the binder is comprised of a water dispersible polymer.

7. The system of claim 6, wherein the water dispersible polymer binder is comprised of a polyacrylate.

8. The system of claim 2, wherein the composition comprises a dye which maintains its characteristic color in the presence of a vaporized chemical sterilant in combination with the component which is chromatically transformed by the action of the vapor phase sterilization treatment.

9. The system of claim 8, wherein the dye which maintains its characteristic color is selected from the group consisting of phthalo green, 613 red, arylide yellow and black oxide.

10. The system of claim 2, wherein the support to which the composition is applied is a paper based or polymeric based substrate.

11. The system of claim 10, wherein the substrate has been applied to a medical instrument.

12. The system of claim 2, wherein the support to which the composition has been applied comprises a medical instrument.

13. A color change composition useful in indicating vapor sterilization, comprising:

an aqueous dispersion of a first dye sufficient to produce a workable color indication when applied to a suitable substrate, the coloring ability of which is substantially altered or destroyed permanently in the presence of a vaporized chemical sterilant, and with the first dye comprising a metallized reactive dye or a cyanine dye; and a dispersion of a second dye or pigment in an amount sufficient permanently to maintain its characteristic color in the presence of the vaporized chemical sterilant.

14. The color change composition of claim 13, wherein the dye is a cyanine dye.

15. The color change composition of claim 13, wherein the second dye or pigment which maintains its characteristic color is selected from the group consisting of phthalo green, 613 red, arylide yellow and black oxide.

16. The color change composition of claim 13, wherein the first dye comprises a copper diazo dye.

17. A color change composition useful in indicating vapor sterilization, comprising an aqueous dispersion of a first dye sufficient to produce a workable and stable color indication when applied to a suitable substrate, the coloring ability of which is substantially altered or destroyed permanently in the presence of a vaporized chemical sterilant to thereby produce an indication stable either within the vapor sterilization environment or outside the environment, with the dye comprising a metallized reactive dye or a cyanine dye, and which aqueous dispersion further contains a polymeric binder.

18. The color change composition of claim 17, wherein the dye is a cyanine dye.

19. The color change composition of claim 17, wherein the composition further comprises a dispersion of a second dye or pigment in an amount sufficient to maintain its characteristic color in the presence of the vaporized chemical sterilant.

20. The color change composition of claim 17, wherein the first dye comprises a copper diazo dye.

21. A process for indicating that an article has been subjected to sterilization, which comprises:

providing an article having affixed thereto a composition comprising a component which is chromatically transformed by the action of a vapor phase sterilization treatment, with the component comprising a metallized reactive dye or a cyanine dye, and subjecting the article to vapor sterilization by means of a vaporized chemical sterilant and thereby effecting chromatic transformation of the component.

22. The process of claim 21, wherein the vapor chemical sterilant comprises hydrogen peroxide.

23. The process of claim 21, wherein the vapor sterilization process comprises using vaporous hydrogen peroxide in combination with ionizing plasma.

24. The process of claim 21, wherein the vapor sterilization comprises using vaporous hydrogen peroxide in combination with peracetic acid and ionizing plasma.

25. The process of claim 21, wherein the component which is chromatically transformed comprises a copper diazo dye.

* * * * *